US006881398B2

(12) United States Patent
Myrman et al.

(10) Patent No.: US 6,881,398 B2
(45) Date of Patent: Apr. 19, 2005

(54) THERAPEUTIC DRY POWDER PREPARATION

(75) Inventors: Mattias Myrman, Stockholm (SE); Per-Gunnar Nilsson, Malmö (SE)

(73) Assignee: Microdrug AG, Hergiswil NW (CH)

( * ) Notice: Subject to any disclaimer, the term of this patent is extended or adjusted under 35 U.S.C. 154(b) by 113 days.

(21) Appl. No.: 10/134,597

(22) Filed: Apr. 30, 2002

(65) Prior Publication Data

US 2003/0192540 A1 Oct. 16, 2003

(30) Foreign Application Priority Data

Apr. 12, 2002 (SE) .............................................. 0201125

(51) Int. Cl.[7] ............................ A61K 9/00; A61K 9/14; A61K 9/12; A61M 15/00

(52) U.S. Cl. ........................... 424/45; 424/46; 424/489; 424/499; 128/203.15; 128/203.23; 514/2; 514/3

(58) Field of Search ............................ 424/45, 46, 489, 424/499; 514/2, 3; 128/203.15, 203.23, 315; 131/271

(56) References Cited

U.S. PATENT DOCUMENTS

| | | | | |
|---|---|---|---|---|
| 5,408,994 A | | 4/1995 | Wass et al. | |
| 5,441,060 A | * | 8/1995 | Rose et al. | 131/271 |
| 5,469,843 A | | 11/1995 | Hodson | |
| 5,655,523 A | | 8/1997 | Hodson et al. | |
| 5,714,007 A | | 2/1998 | Pletcher et al. | |
| 5,857,456 A | | 1/1999 | Sun et al. | |
| 6,074,688 A | | 6/2000 | Pletcher et al. | |
| 6,089,227 A | | 7/2000 | Nilsson | |
| 6,524,557 B1 | * | 2/2003 | Bäckström et al. | 424/46 |
| 2003/0192539 A1 | * | 10/2003 | Myrman | 128/203.15 |

FOREIGN PATENT DOCUMENTS

| | | |
|---|---|---|
| WO | 02/11803 A1 | 2/2002 |
| WO | 02/18000 A1 | 3/2002 |

* cited by examiner

*Primary Examiner*—Gary Kunz
*Assistant Examiner*—Mina Haghighatian
(74) *Attorney, Agent, or Firm*—Young & Thompson

(57) ABSTRACT

A therapeutic dry powder preparation and a method of administering such a preparation are disclosed for effectively de-aggregating and dispersing into air a dose of medication powder in an administration the dose to a user. The present dry powder preparation and method do not require other sources of energy besides the power of an inhalation effort by a user to produce a very high degree of de-aggregation and efficient dispersal into air of the dry powder medication dose. Utilizing an effort of sucking air through a nozzle, the particles of the therapeutic powder dose, made available to the nozzle, are gradually de-aggregated and dispersed into a stream of air entering the nozzle. The gradual de-aggregation and dispersal is produced by an air-razor effect due to a relative motion introduced between the nozzle and the powder dose

76 Claims, 15 Drawing Sheets

A-A

```
┌─────────────────────────────┐
│    Select a dry powder      │
│       formulation           │
└─────────────┬───────────────┘
              ▼
┌─────────────────────────────┐
│   Form a dose from the      │
│      selected powder        │
└─────────────┬───────────────┘
              ▼
┌─────────────────────────────────────┐
│ Give the dose an extended contour,  │
│  excellent porosity and dosing      │
│ qualities for a successful,         │
│ continuous administration by        │
│ inhalation                          │
└─────────────┬───────────────────────┘
              ▼
┌─────────────────────────────────────┐
│ Implement an Air razor method for   │
│ de-aggregation and dispersal of the │
│   dose into the inhaled air         │
└─────────────┬───────────────────────┘
              ▼
┌─────────────────────────────────────┐
│ Deliver the dose continuously to    │
│ the airways of the user during an   │
│ inhalation, whereby the delivered   │
│ dose is composed of a majority by   │
│ mass of fine particles              │
└─────────────────────────────────────┘
```

Fig. 18

THERAPEUTIC DRY POWDER PREPARATION

TECHNICAL FIELD

The present invention relates to the use of inhaled drugs in treatment of human disorders and presents a therapeutic dry powder preparation and a method and a system for de-aggregation and dispersal into air of the preparation forming a medicinal formulation in connection with an administration to a user inhaling through a dry powder inhaler device, the powder comprising at least one pharmacologically active substance in the form of a finely divided dry powder.

BACKGROUND

The dosing of drugs is carried out in a number of different ways in the medical service today. For a number of reasons, such as local treatment of lung diseases, replacement of injection therapy and for rapid onset of action, there is a large interest in administering drugs to the lungs of a patient. A number of different devices have been developed in order to deliver drugs to the lung,; e.g. pressurized aerosols (pMDIs), nebulisers and dry powder inhalers (DPIs).

While inhalation of drugs already is well established for local treatment of lung diseases such as asthma, much research is going on to utilize the lung as a feasible entry into the body of systemically acting drugs. For locally acting drugs, the preferred deposition of the drug in the lung depends on the localization of the particular disorder and depositions in the upper as well as the lower airways are of interest. For systemic delivery of the medication, a deep lung deposition of the drug is preferred and usually necessary for maximum efficiency. With deep lung should be understood the peripheral lung and alveoli, where direct transport of active substance to the blood can take place.

The lung is an appealing site for systemic delivery of drugs as it offers a large surface area (about 100 $m^2$) for the absorption of the molecules across a thin epithelium thereby giving potential for rapid drug absorption. Pulmonary delivery therefore has the advantage, compared to nasal delivery, that it is possible to obtain a sufficiently high absorption without the need of enhancers. The feasibility of this route of administration is for a particular drug depends on, for example, dose size and extent of absorption for the particular substance.

The critical factors for the deposition of inhaled particles in the lung are inspiration/expiration pattern and the particle aerodynamic size distribution. For maximum lung deposition, the inspiration must take place in a calm manner to decrease air speed and thereby reduce deposition by impaction in the upper respiratory tracts.

For dry powder inhalers there are restrictions on the aerodynamic particle size of the drug particles to obtain an acceptable deposition of the drug within the lung. If a particle is to reach into the deep lung the aerodynamic particle size should typically be less than 3 $\mu$m, and for a local lung deposition, typically about 5 $\mu$m. Larger particle sizes will easily stick in the mouth and throat. Thus, regardless of whether the objective is a local or systemic delivery of a drug, it is important to keep the aerodynamic particle size distribution of the dose within tight limits to ensure that a high percentage of the dose is actually deposited where it will be most effective.

De-Aggregation

Powders with a particle size suitable for inhalation therapy have a tendency of aggregating, in other words to form smaller or larger aggregates, which then have to be de-aggregated before the particles enter into the airways of the user. De-aggregation is defined as breaking up aggregated powder by introducing energy e.g. electrical, mechanical, pneumatic or aerodynamic energy. Some dry powder inhalers rely on external sources of de-aggregating power e.g. mechanical, electrical or pneumatic, yet some rely only on the power provided by the user's inspiration.

The aerodynamic particle diameter is the diameter of a spherical particle having a density of 1 $g/cm^3$ that has the same inertial properties in air as the particle of interest. This means that the aerodynamic particle size is determined by the primary particle size, the shape of the particle and the particle density. If primary particles are incompletely de-aggregated in the air, the aggregate will aerodynamically behave like one big particle. Hence, for a particular drug substance there are three major, principally different ways to vary the aerodynamic particle size distribution from a dry powder inhaler, DPI, by a) varying the primary particle size distribution or b) by varying the degree of de-aggregation or c) by varying the particle density (making a particle look like tumbleweed).

Current inhalation devices, intended for asthma and other lung diseases, normally deliver the aerosolized drug in an aerodynamic size range suitable for local lung deposition. This aerodynamic particle size distribution is often caused by an inefficient de-aggregation of powder with a primary particle size in the range 2–3 $\mu$m. Thus, the inhaled dose largely consists of aggregates of particles. This has several disadvantages, the most important being:

The uniformity of aerodynamic particle size distribution between different doses may vary considerably, because the de-aggregation is sensitive to slight differences in inspiration conditions from one inhalation to the next.

Particle size distribution of the delivered dose may have a tail of large aggregates, which will deposit in the mouth and upper airways.

A better, more robust situation is obtained with a high degree of de-aggregation of the medication powder in the inhaled air as a good de-aggregation gives a better repeatability and efficiency of drug deposition in the lung. Preferably, the de-aggregating system should be as insensitive as possible to the inhalation effort produced by the user, such that the delivered aerodynamic particle size distribution in the inhaled air is independent of the inhalation effort.

Hence, for an efficient delivery of drugs to the lung there is a need for a system consistently generating a very high degree of de-aggregation of the medication powder when the patient inhalation effort is varied within reasonable limits. This is obvious for systemically acting drugs where a deep lung deposition is needed, but also for locally acting drugs, where a more local lung deposition is preferred, a consistent high degree of de-aggregation of the medication powder is advantageous. In this way the aerodynamic particle size distribution will be less dependent upon the users inhalation effort. The average particle size, which influences the deposition pattern in the lung, can be controlled by the primary particle size distribution of the particles in the powder. Larger primary particle size and excellent de-aggregation offers a robust system for local lung delivery.

A very high degree of de-aggregation presumes the following necessary steps:

a suitable formulation of the powder (particle size distribution, particle shape, adhesive forces, density, etc.)

a suitably formed dose of the powder adapted to the capabilities of a selected inhaler device an inhaler device providing shear forces of sufficient strength in the dose to de-aggregate the powder (e.g. turbulence, impaction)

Turning to the drug formulation, there are a number of well-known techniques to obtain a suitable primary particle size distribution to ensure the potential for a correct lung deposition for a high percentage of the dose. Such techniques include jet-milling, spray-drying and super-critical crystallization.

There are also a number of well-known techniques to modify the forces between the particles and in such way obtaining a powder with suitable adhesive forces. Such methods include modification of the particles shape and surface properties of the particles, e.g. porous particles and controlled forming of powder pellets, as well as addition of inert carrier with a larger average particle size (so called ordered mixture).

Most locally acting drugs for inhalation presently on the market are rather small organic molecules. Examples of employed drugs include steroids such as budesonide, broncodilators such as salbutamol and similar substances.

For many of these drug substances, the pharmaceutical formulation development work is rather straightforward. On the other hand, novel drugs both for local and systemic delivery often includes biological macromolecules with completely new demands on the formulation.

A number of proteins and peptides have a potential for being suitable for inhalation therapy and some of them are in various stages of development. Some examples are insulin, alpha-1-proteinase inhibitor, interleukin 1, parathyroid hormone, genotropin, colony stimulating factors, erythropoietin, interferons, calcitonin, factor VIII, alpha-1-antitrypsin, follicle stimulating hormones, LHRH agonist and IGF-I.

Protein and peptide drugs (PPDs) have characteristics that present significant formulation challenges. In particular their chemical and enzymatic lability practically prevents traditional dosage forms such as oral tablets. Therefore PPDs are currently mainly administered parenterally as intravenous, intramuscular or subcutaneous injections. While these routes are normally satisfactory for a limited number of administrations, there are problems with a long-term therapy. Frequent injections, necessary for the management of a disease, is of course not an ideal method of drug delivery and often leads to a low patient compliance as they infringe on the freedom of the patient. Further, many patients are reluctant to inject for psychological reasons and therefore inject with larger time intervals than what is medically desirable.

Insulin is an example of an important peptide drug where frequent parenteral administrations are the most common way of administration. A large percentage, perhaps 5%, of the human population suffers from Diabetes Mellitus. Diabetes is caused by impaired or insufficient insulin production. Normally the blood glucose level is continuously controlled by the natural insulin production of the body, but when this does not happen in the case of diabetes, the glucose concentration may rise to high and maybe life-threatening levels. In such cases insulin in suitable quantities must be externally supplied for management of the disease.

Self-administration of insulin is an important reality and part of everyday life for many patients with diabetes. Normally, the patient needs to administer insulin several times daily. Insulin given orally has not been effective because insulin is degraded in the gastrointestinal tract resulting in systemic concentrations too low for therapeutic effect.

The most common method of insulin administration is subcutaneous injection by the patient based on close monitoring of the glucose level. As mentioned above, frequent injections are not an ideal method of drug delivery. Further, there are pharmacokinetical limitations when using the subcutaneous route. Absorption of insulin after a subcutaneous injection is rather slow. It sometimes takes up to an hour before the glucose level in the blood begins to be significantly reduced. This inherent problem with subcutaneous insulin delivery cannot be solved with a more frequent administration. To obtain plasma insulin concentrations that are physiologically correct it is necessary to choose another route of administration.

Delivery of protein and peptide drugs (PPDs) through nasal passage generally gives a rather low and variable bioavailability. Factors affecting the bioavailability from the nasal cavity include the limited surface area (approximately 150 $cm^2$), the large molecular size of the PPDs, mucocilliary clearance and enzymatic degradation. With the help of absorption enhancing agents the absorption of PPDs from the nasal cavity can be significantly improved. A rather large number of enhancers have been tested and suggested mechanisms are that they open the tight junctions, disrupt membrane or inhibits enzymes. However, penetration enhancers often cause local irritation on the nasal membrane, a problem that has proved difficult to solve.

Delivery by inhalation of aerosolized insulin is documented as far back as in the 1920's (M. Gänsslen "Über Inhalation von Insulin"). The natural state for insulin as a medical substance is still in solution-form, so that historically from the 1920's onwards research into nasal and pulmonary administration of insulin has been concentrated to various liquid formulations of insulin.

Methods to manufacture dry powder insulin from a liquid state has been known and applied for more than 50 years, including such methods as evaporation, spray-drying and freeze-drying. However, reliable and economic technologies have been lacking for on one hand producing insulin powders with suitable properties and on the other hand suitable apparatuses for delivering the powder to the user in a way that ensures an effective systemic delivery. This has prevented the main-stream research from using insulin in dry powder formulations. However, in the early 1990's Bäckström, Dahlbäck, Edman and Johansson (Therapeutic preparation for inhalation WO 95/00127) showed that inhalation of a therapeutic preparation comprising insulin and an absorption enhancer quickly and efficiently leads to insulin being absorbed in the lower respiratory tract. It is evident that the enhancer was necessary probably because of insufficient de-aggregation of the powder and the use of an inferior dry powder inhaler. During the last decade a number of reports describing the pharmacokinetics and pharmacodynamics of insulin delivered to the lung of humans have been published. In most reported cases, the insulin has been nebulised from an aqueous preparation. However, in the early 1990's some research into the effect of pulmonary administration of insulin in dry powder form was performed. It has been demonstrated that systemic delivery of dry insulin powder can be accomplished by oral inhalation and that the powder can be rapidly absorbed through the alveolar regions of the lung. For instance, in U.S. Pat. No. 5,997,848 it is demonstrated that systemic delivery of dry insulin powder is achieved by oral inhalation and that the powder can be rapidly absorbed through the alveolar regions of the lungs. However, dose resolution still seems to be low. According to the disclosure, the insulin dosages are having a total weight from a lowest value of 0.5 mg up to 10–15 mg of insulin and the insulin is present in the individual particles at from only 5% up to 99% by weight with an average size of the particles below 10 µm.

A number of factors make delivery of PPDs to the lung as dry powders an attractive option. PPDs are susceptible to several paths of degradation including deamidation, hydrolysis and oxidations. Therefore, an acceptable stability of the pharmaceutical product can be a difficult task in many cases. From a stability point of view, a solid formulation stored under dry conditions is normally the best choice. In the solid state, these molecules are normally relatively stable in the absence of moisture or elevated temperatures. Proteins and peptides of moderate molecular weights are soluble in the fluid layer in the deep lung and dissolve therefore ensuring rapid absorption from the lung.

Turning to the presentation of the dose, two main classes of dry powder systems are available on the market, the reservoir type where the powder is present in the inhaler as a bulk, and the single dose type where the powder is pre-metered into single doses. In the first case, the dose is metered off by the patient using the device, while in the second case the dose has been metered off and enclosed into for example gelatin capsules or Al-blister by the manufacturer.

A special case of pre-metered doses is the electrostatically or electro-dynamically manufactured doses, see our U.S. Pat. No. 6,089,227 and our Swedish Patents SE 9802648-7, SE 9802649-5 and SE 0003082-5. See also U.S. Pat. Nos. 6,063,194, 5,714,007, 6,007,630 and the International Application WO 00/22722. The contour of a dose manufactured in this way can be tailored to suit a particular application. In addition, there are also large opportunities to tailor the internal powder structure, such as porosity, which will influence the adhesion forces between the particles.

A large number of different concepts to de-aggregate the drug powder in DPIs have been developed. One example is the use of a spacer, which is based upon having the aerosolized particles distributed evenly in a container from which the inhalation can take place. In principle an inhaler is coupled to a container having a relatively large volume and into which a powder aerosol is injected. Upon inhalation from the spacer the aerosolized powder will effectively reach the alveoli. This method in principle has two drawbacks, firstly difficulties to control the amount of medicine emitted to the lung as an uncontrolled amount of powder sticks to the walls of the spacer and secondly difficulties in handling the relatively space demanding apparatus.

External sources of energy to amplify the inhalation energy provided by the user during the act of inhalation are common methods in prior art inhalers for improving the performance in terms of de-aggregation. Some manufacturers utilize electrically driven propellers, piezo-vibrators and/ or mechanical vibration to de-aggregate the agglomerates. The addition of external sources of energy leads to more complex and expensive inhalers than necessary, besides increasing the demands put on the user in maintaining the inhaler.

Hence, there is a demand for suitable therapeutic preparations of medication substances and a method and for providing a highly effective de-aggregation and dispersal into air of a medication powder in connection with administration to a user inhaling through a new type of inhaler device.

SUMMARY

A therapeutic dry powder preparation in the form of a metered medication dose intended for inhalation into the airways of a user to provide local or systemic treatment, depending on the disorder, and a method for effectively de-aggregating and dispersing into air a dose of medication powder and more specifically a method and a system of administering the dose of medication powder to a user are disclosed.

In contrast to prior art, the present invention does not require other sources of energy besides the power of the inhalation effort by the user to produce a very high degree of de-aggregation and efficient dispersal into air of a dry powder dose.

In order to obtain a very high degree of de-aggregation and dispersal into air of the dose when it is made available and released to a user inhaling through a new type of inhaler, the powder in the dose must present a suitable porosity. The powder preparation used in the dose forming process must also provide a suitable aerodynamic particle size distribution for the intended medicinal application. The powder is preferably metered off using electrostatic or electrodynamic field methods or a combination, but other methods of dose forming are equally possible. Preferably, an extended dose will be obtained in the dose forming process offering a tailored size and contour as well as appropriate porosity and inter-particular adhesion forces.

De-aggregation and dispersal into air of powder in the dose is provided by a powder Air-razor method implemented in the new type of inhaler device. Utilizing an effort by a user of sucking air through the inhaler, the air first passing through a nozzle, the particles in the powder dose, made available to the nozzle, are gradually de-aggregated and dispersed into the stream of air entering the nozzle. The gradual de-aggregation and dispersal will be produced by a relative motion introduced between the nozzle and the extended dose. In a preferred embodiment, the powder is deposited onto a substrate member, the accumulated powder of the extended dose generally occupying a larger area than the area of the nozzle inlet aperture. The nozzle is at the beginning preferably positioned outside the powder area, not accessing the powder by the relative motion until the air stream into the nozzle, created by the suction, has passed a threshold flow velocity. Coincidental with the application of the suction by the user, or shortly afterwards the relative motion will begin such that the nozzle traverses the powder dose area gradually. The high velocity air going into the nozzle inlet aperture provides plenty of shearing stress, turbulence and inertia energy as the flowing air hits the first leading point of the border of the extended dose contour. The particles in the particle aggregates of the powder adjacent to the inlet aperture of the moving nozzle are thus released, de-aggregated to a very high degree as well as dispersed and subsequently entrained in the created air-stream going through the nozzle and further into the airways of the user.

A preferred method of administering a medication dose of therapeutic dry powder comprising at least one finely divided, pharmacologically active medication substance to a user inhaling through the new type of inhaler depends on selecting a dry powder formulation providing a suitable aerodynamic particle size distribution. Also, for optimum results in the delivery to the user the dose is preferably formed such that it has an extended contour, suitable porosity and dosing qualities for application in an inhaler implementing an Air-razor arrangement. Then, the result will be a delivery of the dose to the targeted site of action in the airways of the user characterized by a continuous dose delivery with a very high degree of particle de-aggregation, whereby the delivered dose is composed of a majority, by mass, of fine particles.

A therapeutic dry powder preparation, suitable for inhalation, comprising finely divided, pharmacologically active substance for application in a new type of inhaler device is set forth by the independent claims 1 and 23 and the dependent claims 2 to 12 and 24 to 31, and a method of administration to the airways of a user of such a therapeutic powder preparation dose by this new type of inhaler device is set forth by the independent claim 13 as well as the dependent claims 14 to 22.

SHORT DESCRIPTION OF THE DRAWINGS

The invention, together with further objects and advantages thereof, may best be understood by referring to the following detailed description taken together with the accompanying drawings, in which:

FIG. 18 illustrates in a flow chart diagram the main steps of the method according to the present invention.

DETAILED DESCRIPTION

The present invention discloses a dose of a therapeutic dry powder preparation as a medication powder, prepared in advance for inhalation, which becomes highly de-aggregated and entrained in inhalation air when applied to a powder Air-razor method of de-aggregating and dispersing the powder particles into air.

The medication powder comprises one or more pharmacologically active substances, such as proteins or peptides, and optionally one or more excipients. In the document the terms "powder" or "medication powder" are used to signify the substance in the form of dry powder, which is the subject of de-aggregation and dispersal into air by the disclosed invention and intended for deposition at a selected target area, the site of action, of a user's airways. Optional excipients may or may not de-aggregate in a similar way as the active pharmacological substance, depending on the design of the powder. For example, an ordered mixture comprises an excipient characterized by particles considerably larger than those of the pharmacologically active substance. Further examples of pharmacologically active substances in dry powder formulations, which are of interest for an administration by inhalation are the following:

Ketobemidone, Fentanyl, Buprenorfin, Hydromorfon, Ondansetron, Granisetron, Tropisetron, Scopolamin, Naratriptan, Zolmitriptan, Almotriptan, Dihydroergotamin, Somatropin, Calcitonin, Erythopoietin, Follicle stimulating hormone (FSH), Insulin, Interferons (alfa and beta), Parathyroid hormone, alfa-1-antitrypsin, LHRH agonist.

Figure 1:
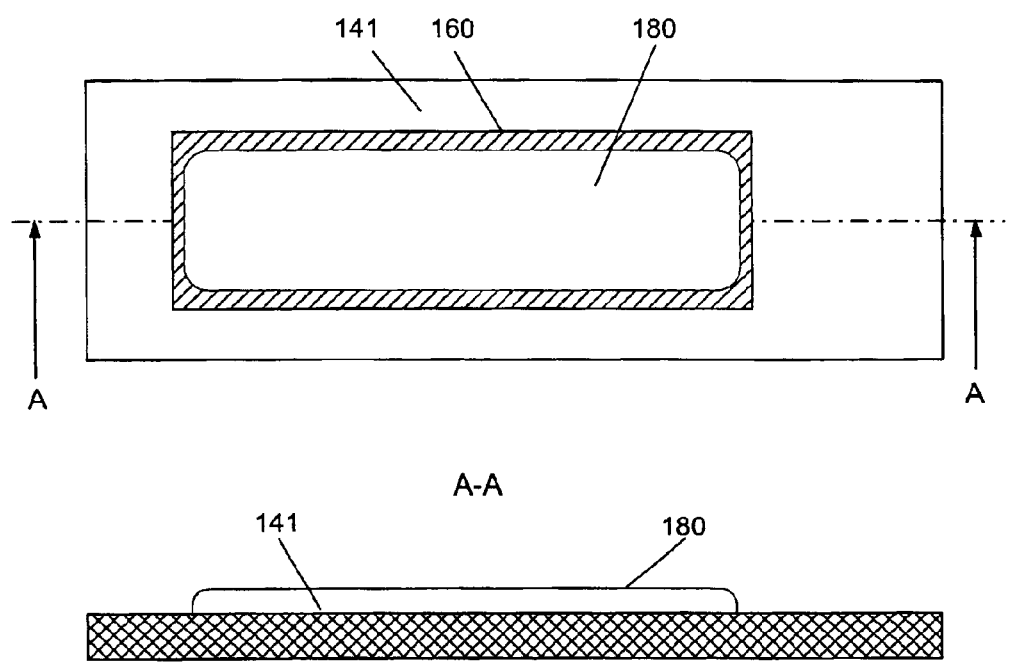
FIG. 1 illustrates in top and side views a metered dose formed as a strip on a target area of a non-perforated substrate member.
Figure 2:
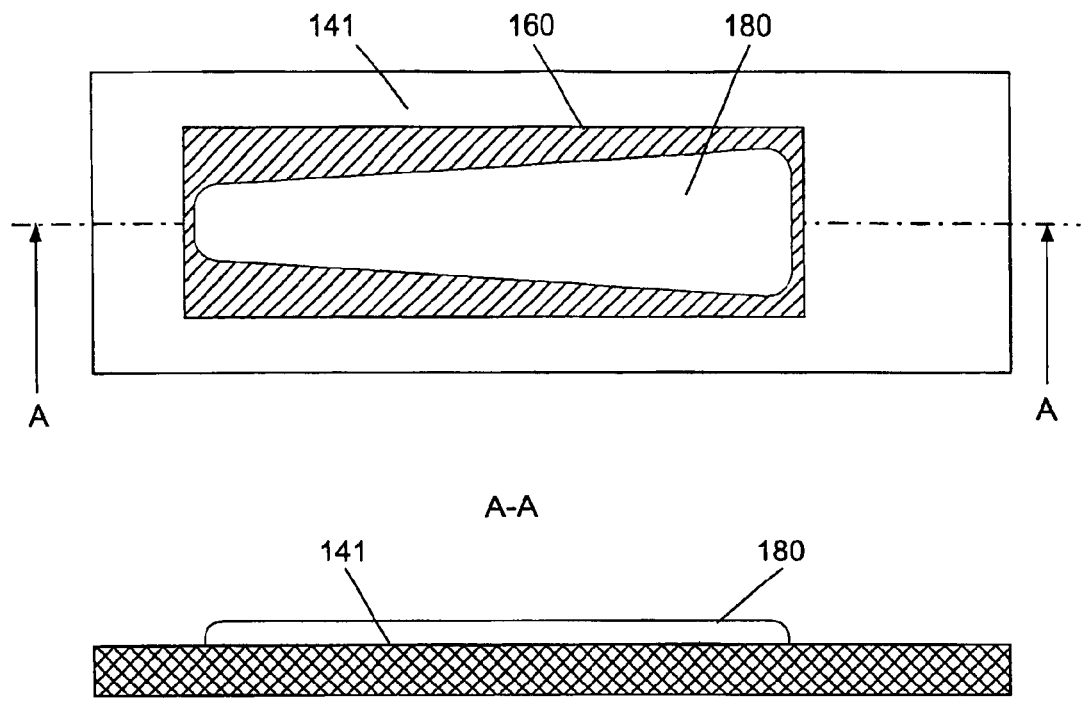
FIG. 2 illustrates in top and side views another metered dose formed as a strip on a target area of a non-perforated substrate member.
Figure 3:
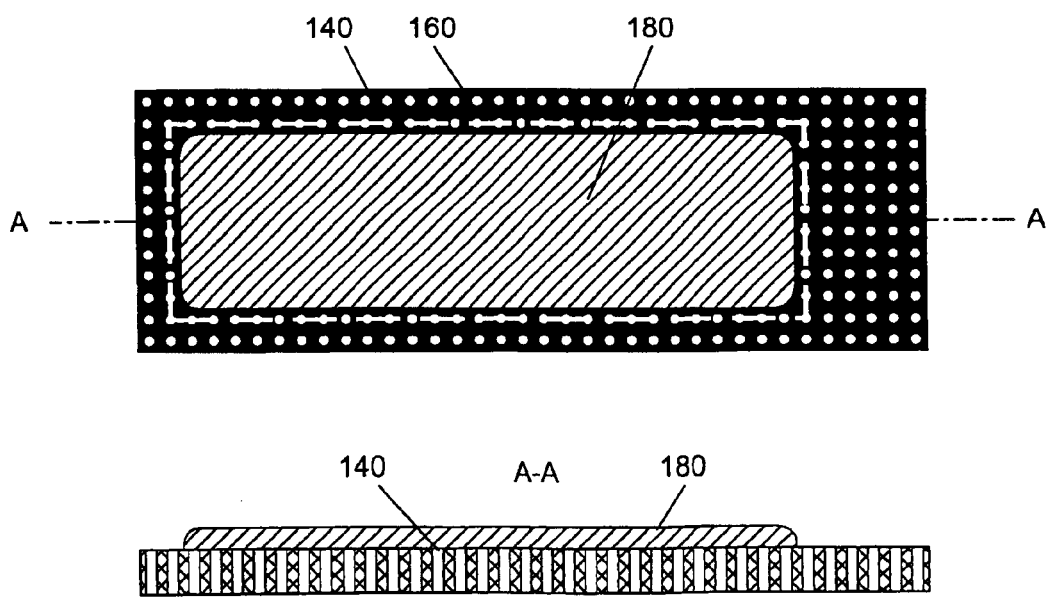
FIG. 3 illustrates in top and side views a metered dose formed as a strip on a target area of a perforated substrate member.
Figure 4:
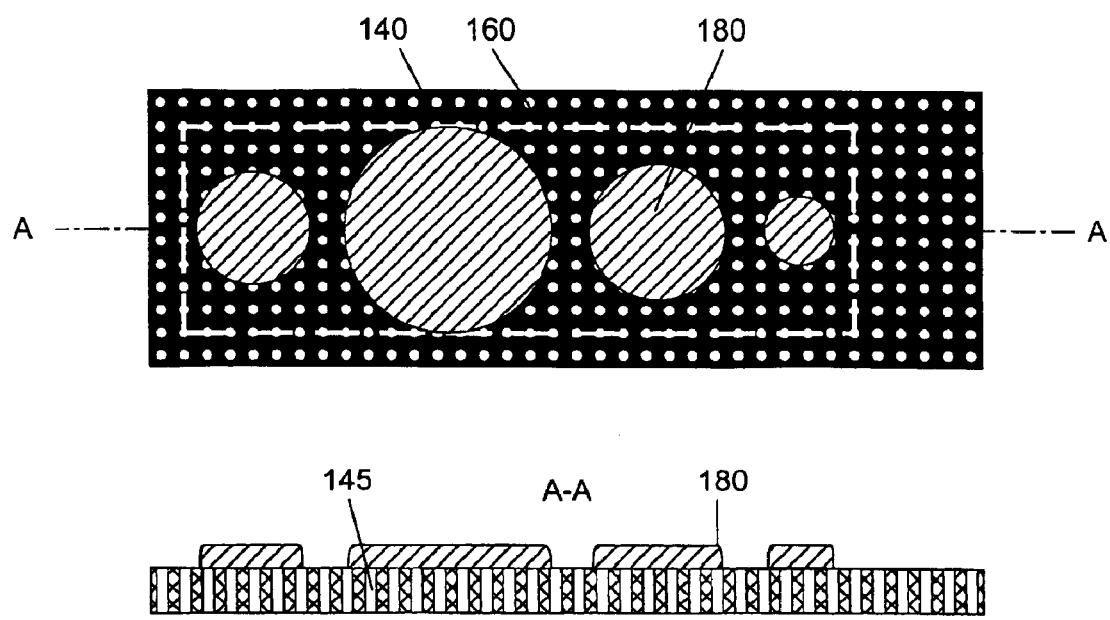
FIG. 4 illustrates in top and side views another metered dose formed as a string of dots onto a target area of a perforated substrate member.
Figure 5:
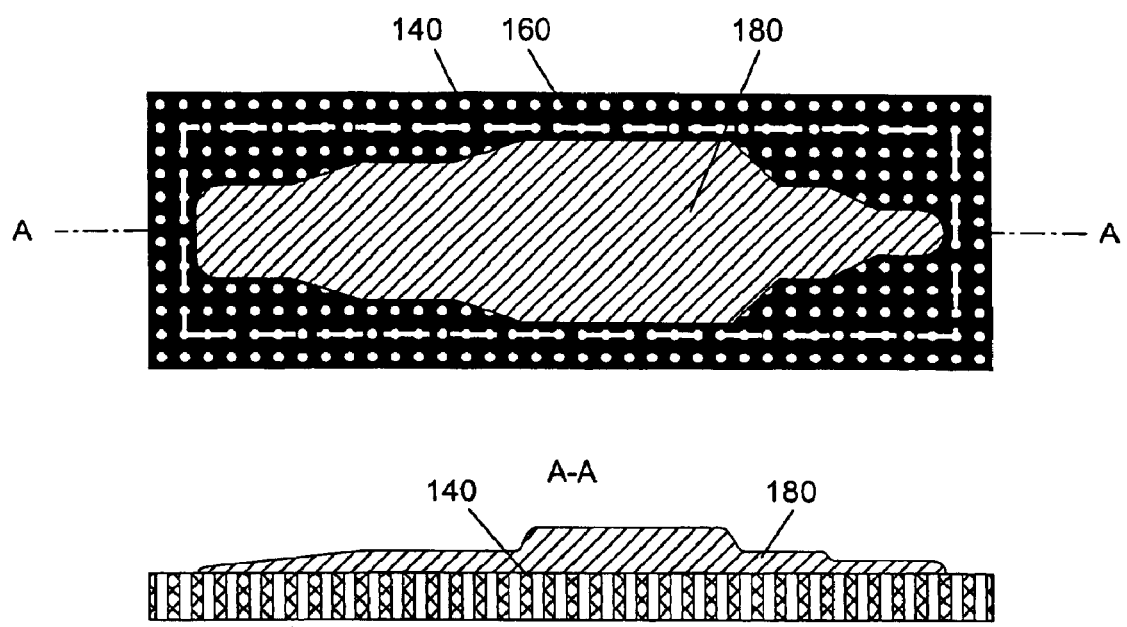
FIG. 5 illustrates in top and side views another metered dose formed as a strip on a target area of a perforated substrate member.
Figure 6:
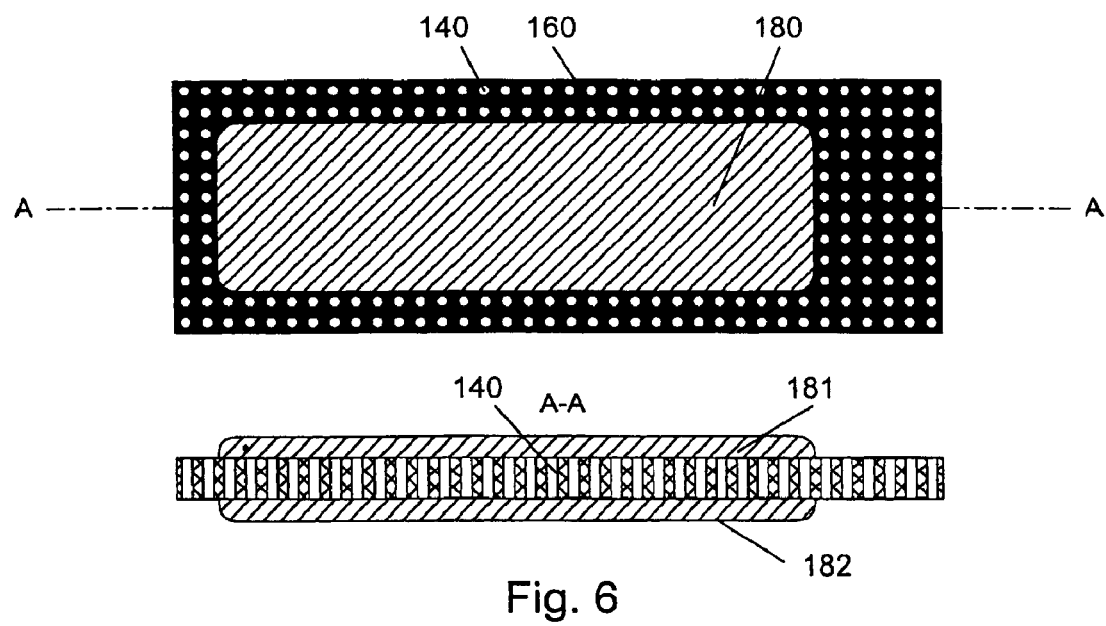
FIG. 6 illustrates in top and side views a metered dose formed as two part-doses on a target area, one on each side of a perforated substrate member.
Figure 7:
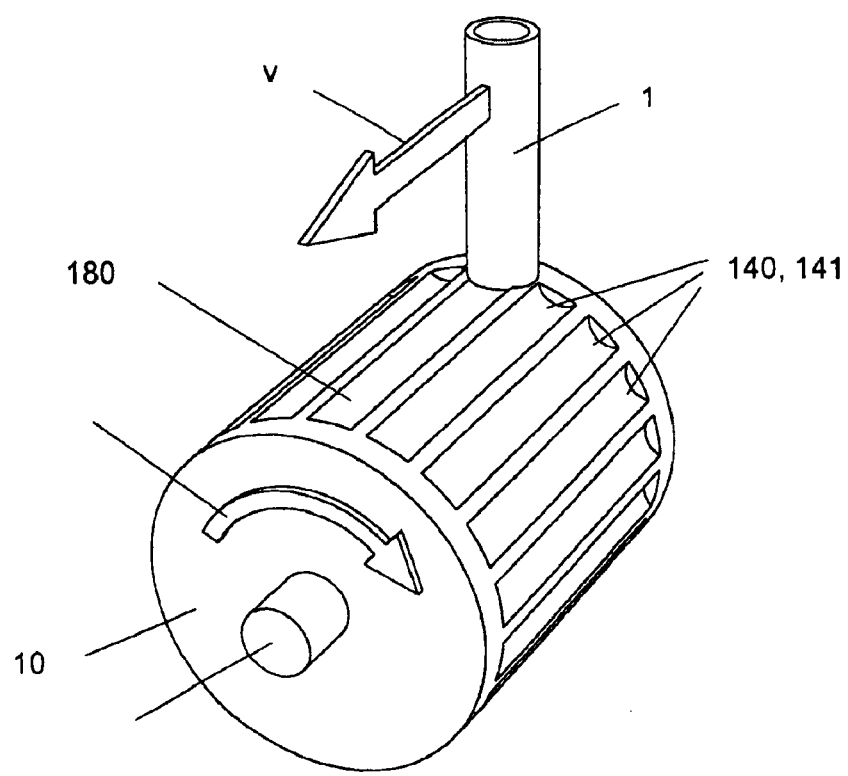
FIG. 7 illustrates a dosing member in the shape of a cylinder with longitudinally arranged multiple dose bed elements.
Figure 8:
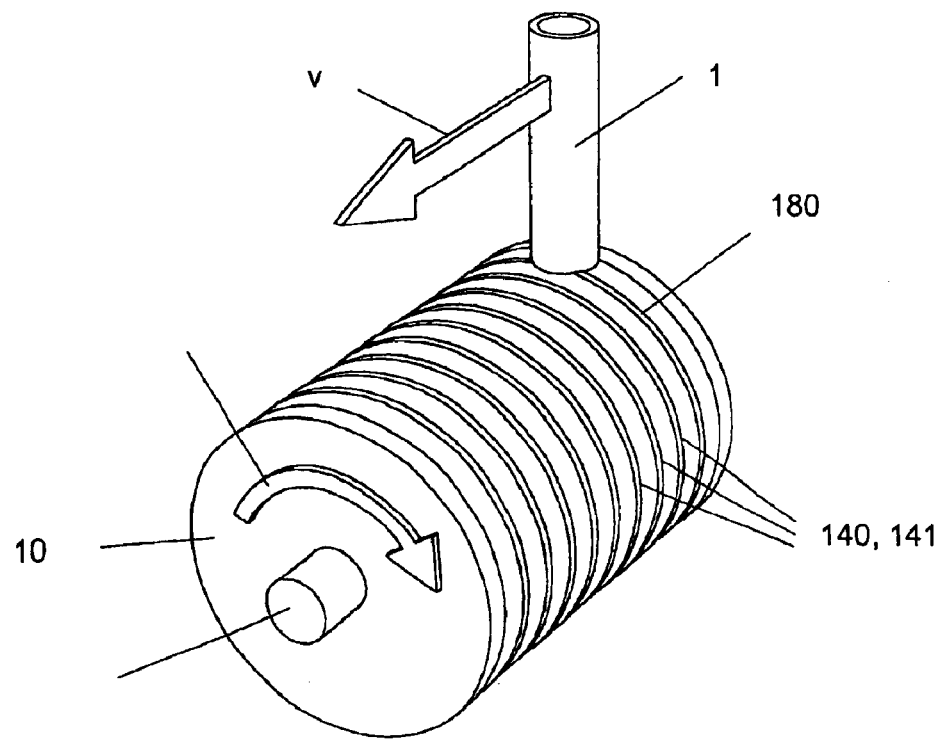
FIG. 8 illustrates a dosing member in the shape of a cylinder with circularly arranged multiple dose bed elements.
Figure 9:
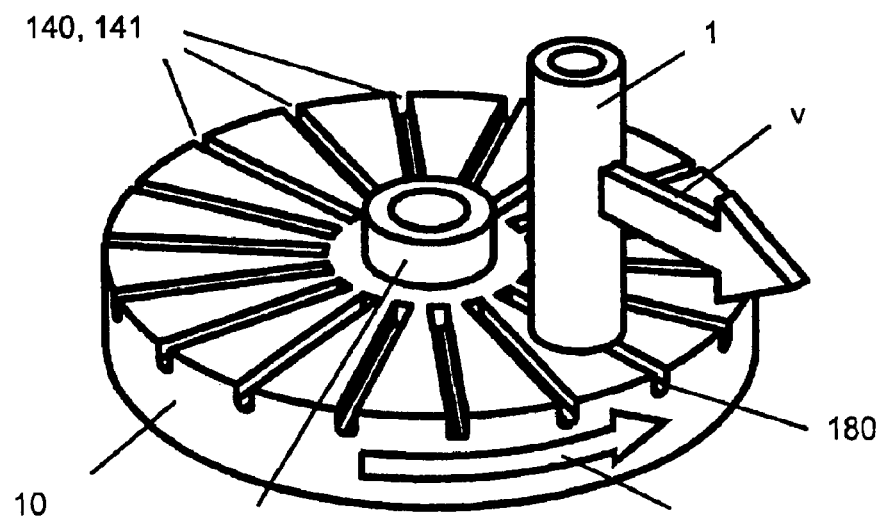
FIG. 9 illustrates a dosing member in the shape of a disc with radially arranged multiple dose bed elements.
Figure 10:
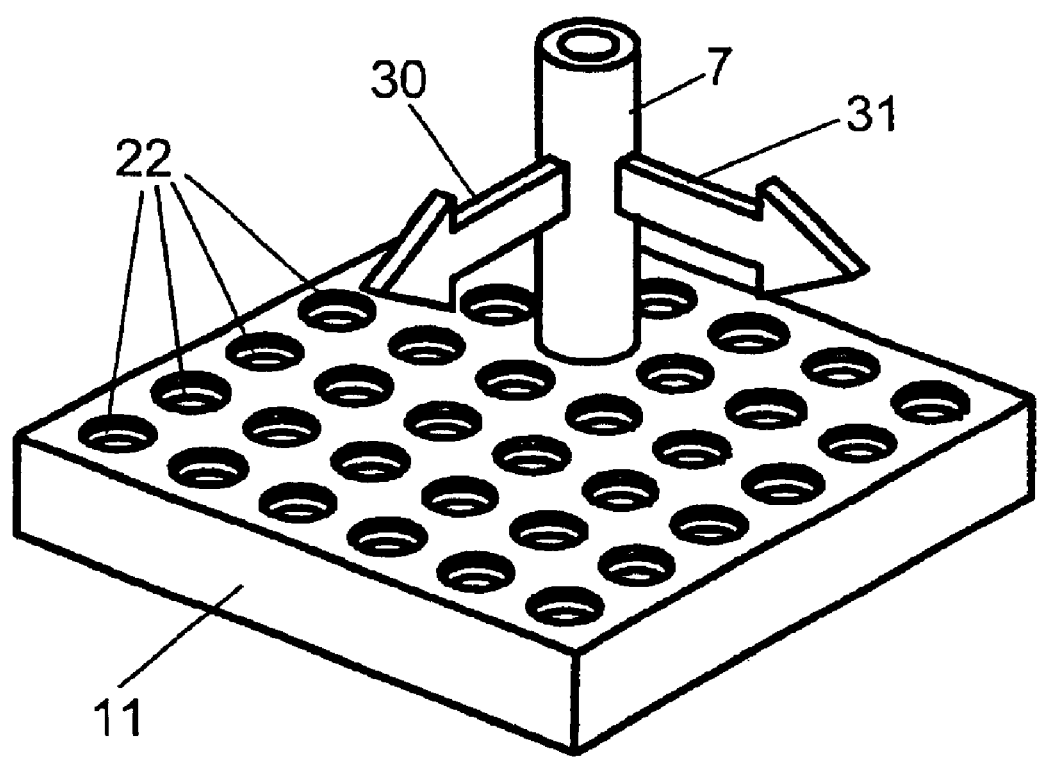
FIG. 10 illustrates a dosing member in the shape of a sheet with circular multiple dose bed elements.
Figure 11A:
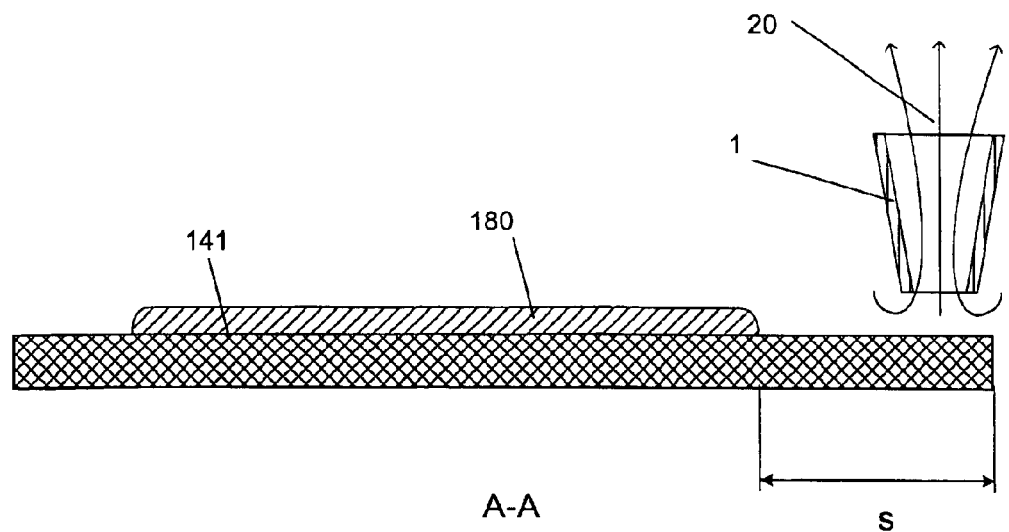
FIG. 11a illustrates in a sectional view an example of a dose on the surface of a non-perforated substrate member and adjacent to the same side as the dose, a nozzle in the starting position before the dose is released.
Figure 11B:
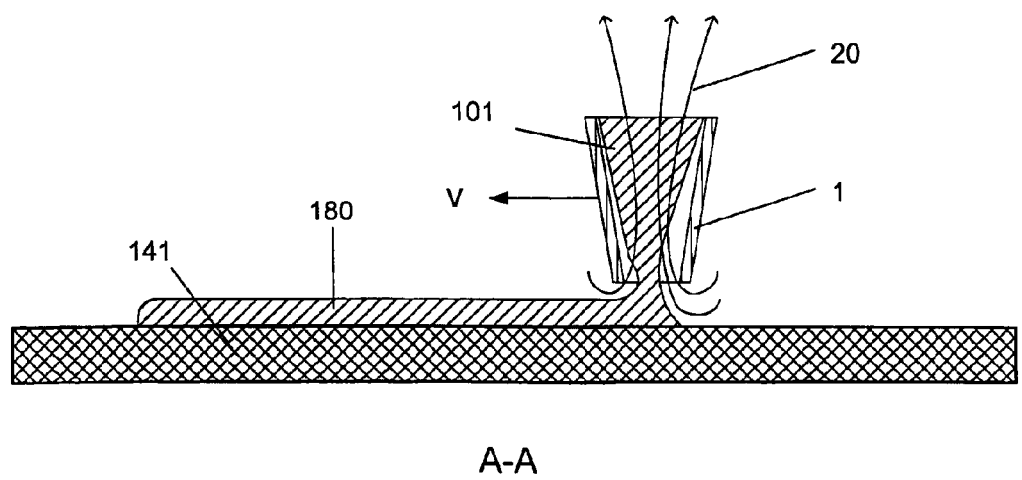
FIG. 11b illustrates in a sectional view an example of a dose on the surface of a non-perforated substrate member and adjacent to the same side as the dose, a moving nozzle sucking up the powder particles dispersed into the air-stream.
Figure 12A:
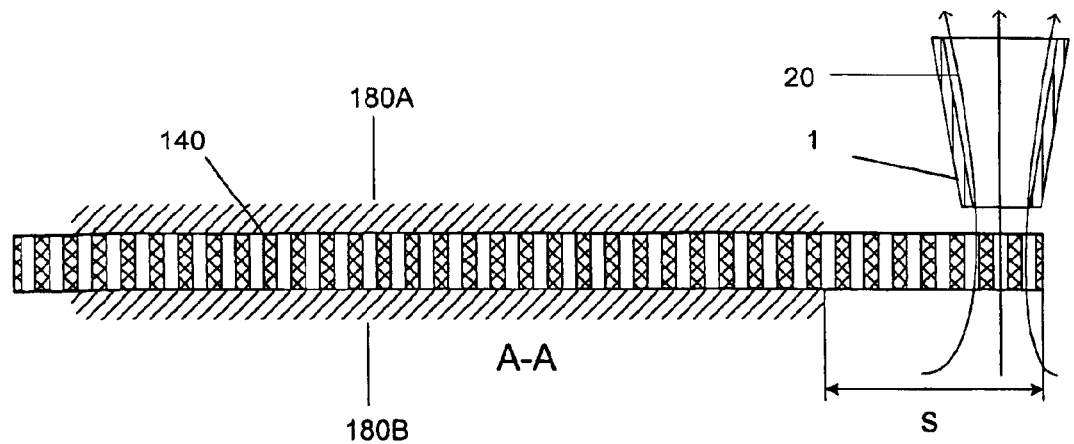
FIG. 12a illustrates in a sectional view an example of a metered dose formed as two part-doses, one on each side of a perforated substrate member and a nozzle adjacent to a first side of the substrate member in a starting position before the dose is released.
Figure 12B:
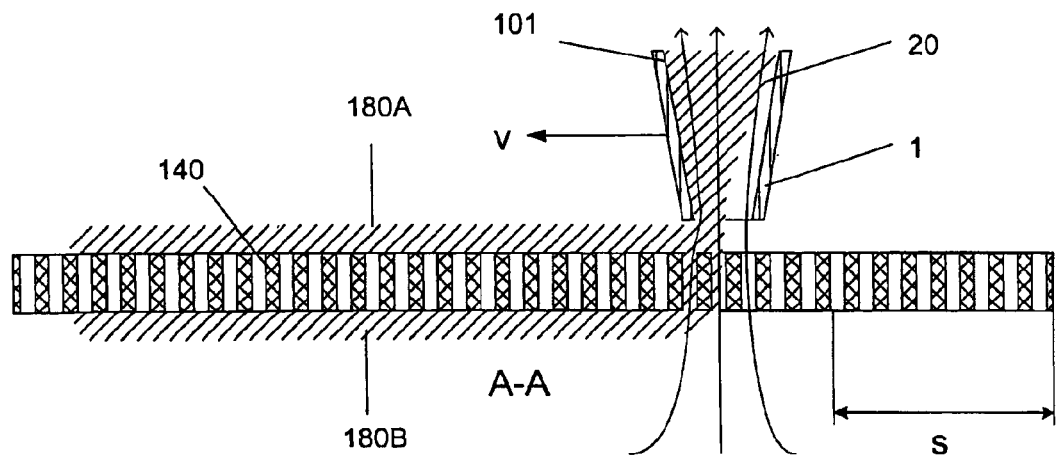
FIG. 12b illustrates in a sectional view an example of a metered dose formed as two part-doses, one on each side of a perforated substrate member and a moving nozzle adjacent to a first side of the substrate member sucking up the powder particles off both sides dispersed into the air-stream.
Figure 13:
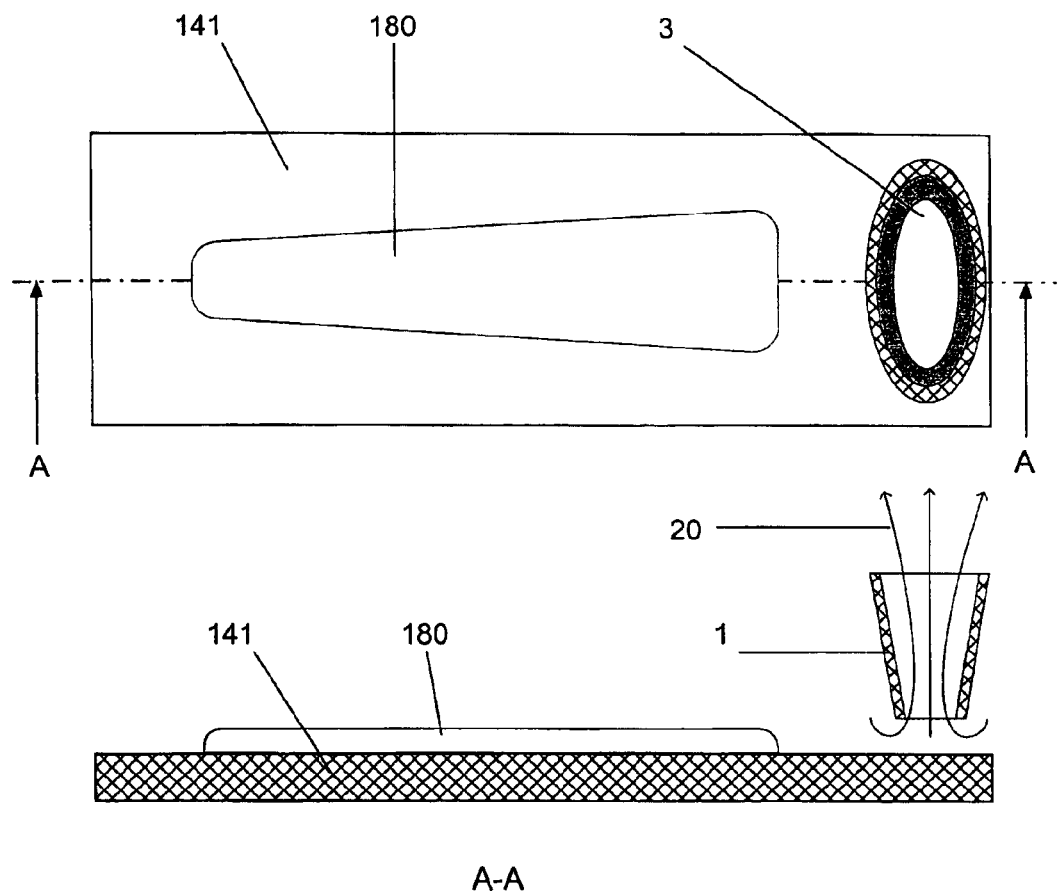
FIG. 13 illustrates a non-porous, non-perforated substrate member with a powder dose onto it and a nozzle with an elliptical inlet aperture adjacent to the same side of the substrate as the dose.
Figure 14:
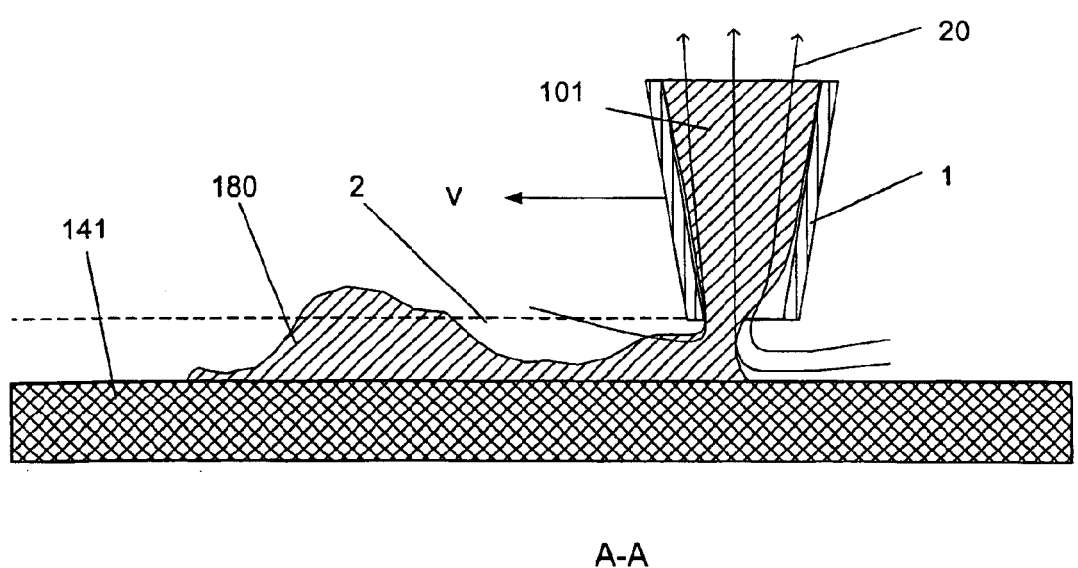
FIG. 14 illustrates a side view of a non-porous, non-perforated substrate member with a powder dose onto it and a nozzle in a line of motion sucking up the powder particles and dispersing them into the air-stream.
Figure 15:
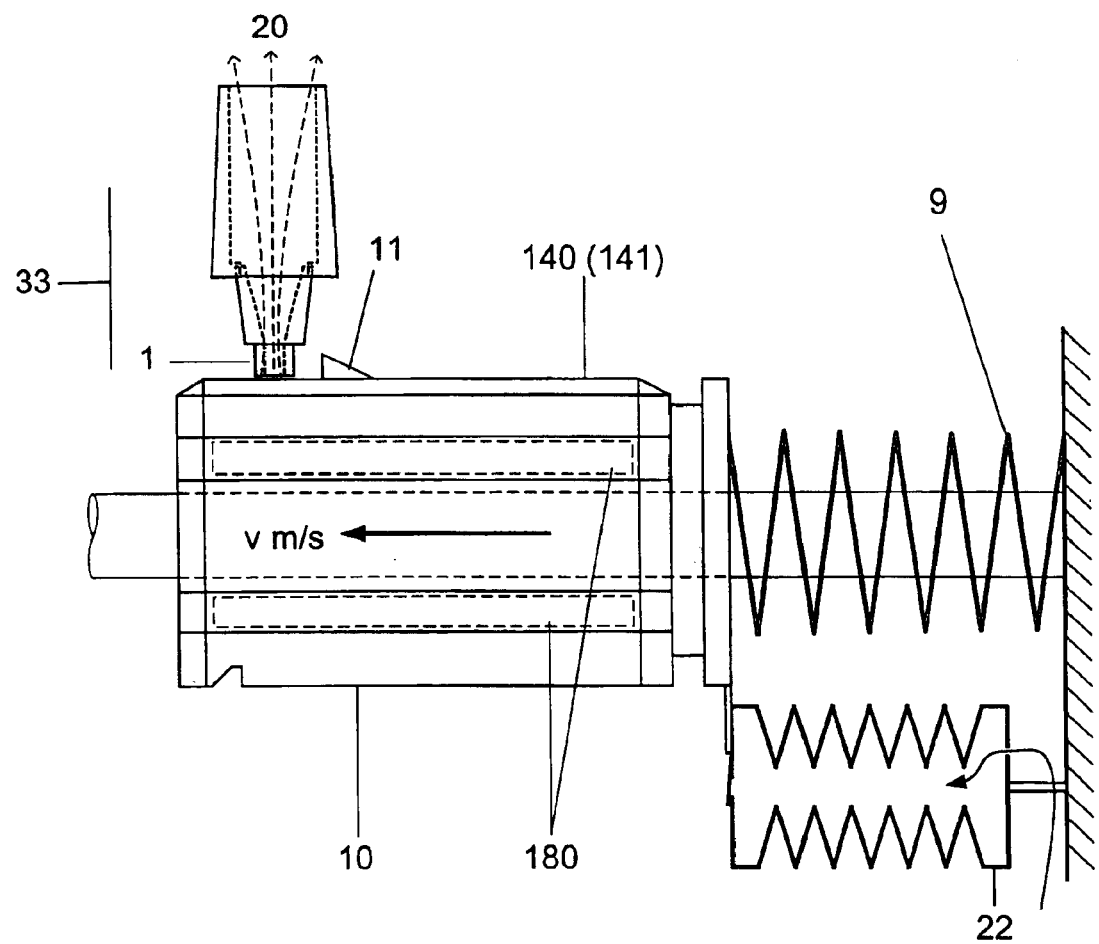
FIG. 15 illustrates an embodiment of a powder Air-razor method showing a nozzle and a dosing member in relative motion to each other in the process of releasing the powder dose.
Figure 16:
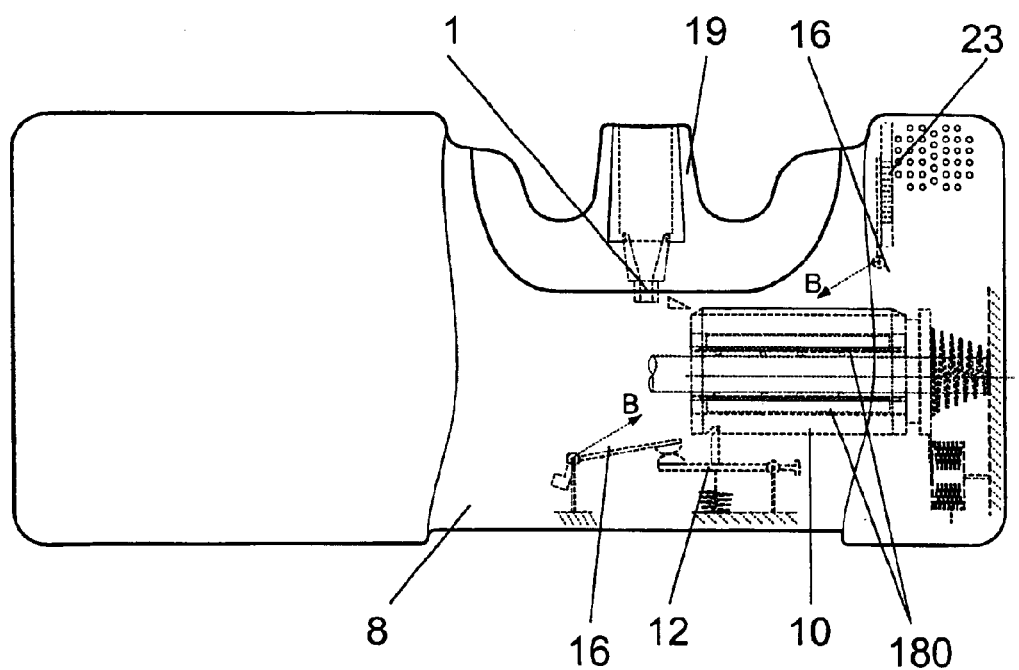
FIG. 16 illustrates an embodiment of an inhaler designed to apply a powder air-razor method.
Figure 17:
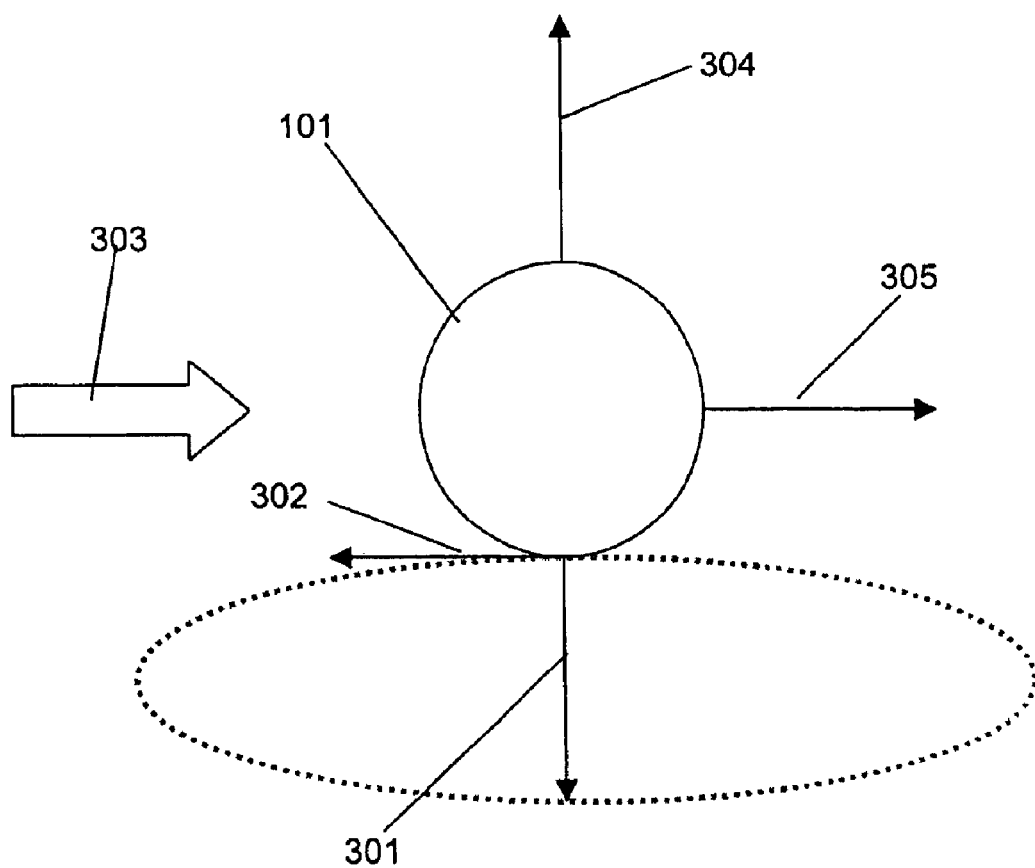
FIG. 17 illustrates the different forces acting on a stationary particle situated in a stream of air.

Referring to FIGS. 1–18 of the drawings wherein like numerals indicate like elements throughout the several views. Six different embodiments of doses onto a substrate member are illustrated in FIGS. 1–6 here offered as examples. Each of FIGS. 1 and 2 illustrates a non-porous, non-perforated substrate member 141 with a selected dose target area 160 onto which a basic extended powder dose 180 in strip form has been deposited, the dose given an arbitrary contour to suit the application. FIGS. 3–6 illustrate similar embodiments to that in FIG. 1, but showing a perforated substrate member 140 instead of a non-perforated substrate member 141. The characteristic difference between a perforated or porous substrate member 140 on the one hand and a non-porous or non-perforated one 141 on the other, is that the former lets air through the substrate including the dose target area 160, while the latter does not let air through. The choice of type of substrate member depends on the application and on the selected inhaler device. The illustrated doses have elongated contours in strip form except FIG. 4, which illustrates an extended dose formed as a series of consecutive spots of equal or varying sizes. The dose bed element 140, 141 may be folded if necessary e.g. in order to put a large dose area into a small allotted space of the dosing member. Different types of dosing members 10, each capable of carrying a multitude of doses are disclosed in FIGS. 7–10. The Air-razor method is illustrated in FIGS. 11a, 11b–where different embodiments of extended doses 180 are combined with different substrate members 140, 141. The drawings illustrate how the relative motion v between the dose and the nozzle 1 lets the shear forces of the airflow into the nozzle inlet aperture de-aggregate and disperse the powder particles 101 gradually into the air 20. FIG. 15 illustrates an embodiment of an Air-razor method implemented in a new type of inhaler, further illustrated in FIG. 16.

In a preferred embodiment, exemplified in FIGS. 11a and 11b, the powder Air-razor method involves the introduction of a controlled relative motion between an extended dose of powder 180, such as insulin, deposited onto a substrate member 141, used as a carrier element for the dose and a suitably arranged nozzle 1, which collects and directs a local high velocity stream of air 20. By pointing the nozzle inlet towards the load of powder on the substrate element, the power of the air-stream, resulting from the suction effort, de-aggregates and disperses into air the particles 101 of the accessed powder on the substrate member. As the nozzle moves in the direction of the extended contour of the deposited powder of the dose, primary particles and particle aggregates are gradually accessed and subjected to the shearing stresses and inertia power of the air-stream going into the nozzle. Thus, the powder Air-razor method sequentially de-aggregates, releases, disperses and entrains individual particles into the air flowing into the nozzle. However, the final medicinal effect depends largely on powder formulation and the characteristics of the primary particles. For optimal medicinal effect the primary particles should be of a certain median size and having a certain size distribution besides being completely de-aggregated when delivered. Only then will a large proportion of the delivered dose settle in the targeted area of the airways of the user, i.e. the site of medicinal action. Delivery may be attained by nasal or oral administration, depending on what type of inhaler device is used.

The degree of particle aggregation and dose porosity play an important role in achieving the best possible fine particle fraction and dispersal into air of the powder as it is forcibly entrained in air as a result of a release process. Finely divided medication powders with primary particle size below 10 μm are rarely free flowing, but to the contrary quite given to forming aggregates. Thus, finely divided powders that are less prone to forming aggregates and/or requiring less energy to break up formed aggregates are preferred in Air-razor applications. For example, porous particles or ordered mixtures may be used to facilitate de-aggregation and dispersion into air of the active substances, which optionally may include pharmacologically acceptable excipients, used e.g. to dilute the active substance or, indeed, to improve one or more qualities of the active substance, such as bioavailability or electrostatic properties.

In contrast to prior art, where the powder in the dose, intended for inhalation, is normally in the form of highly aggregated bulk powder, the dose of the present invention is characterized by a highly porous structure. The interactions, for instance adhesive forces, between different particles are thus much weaker than in prior art. Further, in a preferred embodiment, the dose is also characterized by an extended macroscopic form where the spatial size in at least one dimension is several magnitudes larger than in the other dimensions. These qualities will result in a dose of powder, which is much easier to disperse.

An example of a preferred method of forming a metered dose comprising e.g. PPD's, utilizes an electrostatic or electro-dynamic field deposition process or combinations thereof for depositing electrically charged particles of a medication powder onto a substrate member, such as an electrostatic chuck or a dosing member. The so formed dose presents suitable properties in terms of occupied area, powder contour, particle size, mass, porosity, adhesion etc for easy de-aggregation and dispersal into air by the powder Air-razor method. However, in prior art, other methods of forming a powder dose exist, e.g. mechanical, pneumatic or chemical methods, which are suitable for forming a dose of medication powder and which doses are suitable for a powder Air-razor application. For example, doses may be produced by conventional volumetric or gravimetric metering methods, optionally followed by treating the doses to a supply of energy. The purpose of supplying energy, e.g. by vibrating or giving an impulse, would be to give the dose optimal spatial and porous qualities to be suitable for a powder Air-razor application.

An example of a suitable powder for an inhaler application is an electro-powder. Electro-powder is defined as a prepared dry powder medication substance with or without one or more excipients meeting a set of electrical specifications for optimum electrostatic dose forming properties. For further details, we refer to our Swedish Patent No. SE 0002822-5, which is hereby incorporated herein by reference.

An example of a suitable dose of medication powder, formed onto a substrate member to be used in an inhaler application, is an electro-dose. The term electro-dose, presented in our Swedish Patent No. SE 0003082-5, which is hereby incorporated herein by reference, refers to a dose of pre-metered medicament powder intended for use in a dry powder inhaler. The electro-dose is formed from an electro-powder comprising an active powder substance or a dry powder medicament formulation with or without one or more excipients, the electro-dose being formed onto a substrate member, which is part of a dosing member.

A preferred embodiment of methods of dose forming involves the transfer of charged particles of a medicinal powder emitted from a particle generator to a defined target area of a substrate member. A particle transfer electrode is arranged for forming an electric iris diaphragm and shutter with an associated electric field for the transfer of the electrically charged powder particles from the particle generator to the defined target area of a substrate member to carry a pre-metered powder dose, thereby to control the direction and speed of particles in the dose forming process. The electric iris diaphragm/shutter is located between the particle generator and the substrate such that all particles must pass the iris diaphragm for being transferred to the substrate. This iris diaphragm is also operating as a shutter. By adjusting amplitude and frequency of a superimposed AC potential, charged particles will oscillate in the created AC field such that only small light particles emerge from the iris diaphragm/shutter for further transfer in the dose forming process. Furthermore by the adjustment of amplitude and frequency a majority of charged particles emerging are accelerated and retarded in synchronism with the AC field, such that they impact on a defined target area of the substrate with a low speed and momentum resulting in a desired dose porosity. By moving the substrate member perpendicularly relative to the centerline of the diaphragm/shutter during the dose forming process, an arbitrary geometric extended dose contour onto the substrate member may be brought about. This makes it possible to tailor not only the porosity of the dose but also the dimensions of the dose area, such that the extended dose fits into the selected inhaler and meets the intended medicinal requirements.

The accumulated mass of active medication particles in a dose that are dispersed into inhalation air by the Air-razor method, may be de-aggregated to at least 40% fine particle fraction (FPF) by mass based on the available active medication particles in the powder dose. Preferably, the Air-razor method may be capable of de-aggregating said powder mass to at least 50% FPF and more preferably to at least 60% FPF. The definition of FPF in this context is the fraction of delivered active medication particles by mass with a maximum aerodynamic particle size of 5 $\mu$m.

A dosing member 10 may be executed in many different ways (FIGS. 7–10)to suit different types of inhalers. A dosing member may carry one or more doses on substrate members 140, 141 as described in our Swedish Patent No. SE 504 458 C2, which is hereby included by way of reference. In all cases, suitable substrate members may be selected from electrically conducting, dissipative or insulating materials or combinations of different such materials to give optimum inhalation performance of a metered dose 180 of a particular drug.

Adhesion of Particles

Particles adjacent to other particles or to a substrate member will adhere to each other. Many different types of adhesive forces will play roles in the total adhesive force between a particle and the environment, whether another particle, an aggregate of particles, a substrate member or a combination thereof. The types of adhesive forces acting on a particle can be van der Waal forces, capillary forces, electrical forces, electrostatic forces, etc. The relative strengths and ranges of these forces vary with e.g. material, environment, size and shape of the particle. The sum of all these forces acting on a particle is hereinafter referred to as an adhesive force.

De-Aggregation and Entrainment of Particles

The main objective of the Air-razor method is to de-aggregate and entrain the deposited particles into the air-stream. The particles may be loaded onto a substrate member in many layers in such a way that some particles are in contact with the substrate member whilst others are in contact only with other particles. A complete de-aggregation is to separate all the particles from each other. To separate a particle from its environment involves overcoming the adhesive force as well as the friction force, acting on the particle.

FIG. 26 illustrates forces acting on a particle. The force caused by airflow 303 acting on a particle 101 can be divided into two parts, drag force 305 acting parallel to the airflow, and lift force 304 acting perpendicular to the airflow. The condition for freeing the particle is in the static case that lift and drag forces exceed adhesion 301 and friction 302 forces.

In order to completely, or almost completely, de-aggregate particles, it is not sufficient to let a force act on the particles with enough strength for release and entrainment. If a strong force acts on an aggregate of particles, such that more or less the same force acts on all particles, the aggregate will be entrained into the airflow without de-aggregating. The condition for de-aggregation may thus be stated as: The difference in external forces acting on two particles must overcome the adhesion and friction forces holding them together. Attaining a difference in force from airflow may be done efficiently by creating shear forces, and hence the Air-razor method makes use of high shear forces in the area of the powder deposited for instance onto a substrate member.

To develop high shear stress and thereby high shear forces on the particles, the main principles used by the Air-razor method are:

High velocity of the air-stream

Use of flow streamlines close to a wall

Use of turbulent flow (side effect from high velocity)

Inertia Build-Up

The low-pressure created by the suction through the nozzle drives air to flow in the direction of the low-pressure. Building up inertia means accelerating the mass in a system, i.e. the mass of the air itself, hence giving the desired high velocity airflow after the acceleration period. The velocity of the flow increases to a point where the flow resistance makes further increase impossible, unless the level of low-pressure is decreased, i.e. the pressure drop is increased, or the flow resistance is decreased.

Shear Force Spreading

The area for de-aggregation with high shear forces is concentrated close to the wall of the nozzle. This concentrated area is small compared to the dose area onto a substrate member, especially if the dose comprises finely divided powder of high porosity. Introducing a relative motion between the nozzle and the dose will let the small and concentrated area of high shear stress traverse over the area occupied by the dose. Depending on the actual spatial distribution of the powder in the extended dose and the distance perpendicular to the direction of the motion between the powder and the nozzle inlet aperture, it may occur that the nozzle makes contact with some of the powder. In such case the efficiency of the Air-razor method is not detrimentally affected. Further, the velocity of the airflow will not be affected by the motion of the nozzle in relation to the powder dose, because the speed of the relative motion is very much lower than the velocity of the airflow going into the nozzle inlet. The motion of the nozzle forcibly shifts the position of the driving low-pressure relative the contour of the extended dose in the direction of the motion. Thus, the area of high shear forces moves along a path, controlled by the relative motion of the nozzle, such that the high shear forces gradually disperse powder particles into air. Even if some contact occurs between nozzle and powder, the powder is rapidly dispersed into air without affecting the speed of the relative motion, see FIG. 14 illustrating a case where the line of travel 2 for the nozzle inlet aperture 3 partly contacts the powder 180. Preferably, the path begins just outside a point of contact between the high shear force area of flowing air and the border of the powder dose contour and follows the contour outline from the beginning until the end. The relative motion introduced between the nozzle and the dose of powder is instrumental in attaining and maintaining the desired conditions stated for de-aggregating all of a powder dose and not just part of it. The main advantages given by the relative motion are:

During an initial acceleration phase inertia builds up giving a high velocity airflow Shear forces close to a wall are spread over a large area over time Efficient use of energy Thus, the gradual de-aggregation and dispersal of a medication powder is an inherent essential characteristic of a dose delivery using an Air-razor method.

Efficient Use of Energy

The dosing time interval for de-aggregation and dispersal of powder by an Air-razor method may be selected, depending on the application, within a time frame of an inhalation. Most prior art inhalers will use the inhalation power from the user during a short period only. This means that the total energy used for de-aggregation is correspondingly low in these inhalers, unless external de-aggregation energy is supplied. The time interval for an Air-razor delivery may e.g. be set to 1 second, which means that the inhalation power during this full second is used for de-aggregating particle aggregates.

The first objective for the Air-razor method is to release individual fine particles into air i.e. to overcome the adhesive forces, such as van der Waal, electrostatic, gravity, friction etc, binding a particle to other particles in the aggregates of the powder and/or to the substrate surface. The second objective for the Air-razor method is to direct all airborne particles into the nozzle with as few lost particles as possible. The particles entering the nozzle should then be transported entrained in air to the airways of a user by means of a suitably arranged fluid channel. To fulfill the objectives a source of energy is required. Surprisingly, it has been found that the available drive power from the suction effort by the inhalation of a user provides ample energy for the powder Air-razor method. A normal inspiration effort by an adult user can be shown to produce a low-pressure approximately in a range 1–8 kPa. While a low-pressure in this range is usable, the preferred embodiment uses a range 1–4 kPa for ease of use by most people. Experiments have shown that the limited low-pressure, or drive pressure, thus produced may be used very efficiently, rendering external sources of power unnecessary in the inhalation process. Although the powder Air-razor method works equally well with an external power source, which partially or completely supplies suction power, an external power source does not offer any benefits and is therefore superfluous. However, the relative motion between powder and nozzle, necessary to make use of an Air-razor method, is preferably not powered by the inhalation effort, although this would be entirely possible. Instead, the relative motion may be arranged in many different ways, including e.g. mechanisms comprising spring elements with a capacity for storing potential energy given by the user in handling the inhaler device.

Relatively speaking, in a preferred embodiment the nozzle describes a motion from a start position to an end position, traversing across all of the occupied area of the dose in one stroke. Advantageously, the start position of the nozzle is outside the occupied area by a distance "s" (s≧0+size of nozzle aperture) to allow the suction-initiated airflow to build up through the nozzle to a point before the relative motion brings the nozzle adjacent to the powder. In such a preferred embodiment, the power and shearing stress of the powder Air-razor method is established before it approaches the border of the extended dose contour and begins to attack particle aggregates of the powder. A further improvement of the powder Air-razor method is the introduction of a suction related triggering of the flow into the nozzle, such that the resulting air-speed is sufficiently high to generate the necessary powder Air-razor effect.

By comparison, many prior art inhaler devices begin the powder release cycle by introducing the powder in the channel connecting the air inlet and the final mouthpiece air outlet. The powder is thus surrounded by a volume of stationary air. This considerable volume of air is then accelerated by the suction effort, normally provided by a user, sometimes boosted by added external energy, e.g. by vibrating the medicament powder or giving it an extra puff of pressurized air. All of the powder is subjected to this treatment at the same moment resulting in unsatisfactory de-aggregation of the total powder mass entrained in the air. In short, this means poor efficacy, because not all of the powder is subjected to the necessary shearing stress level for de-aggregation to really happen. Further, because the speed of air surrounding the powder is zero when the release process begins, some of the particle aggregates in the powder will be torn loose during the acceleration phase when the shearing stress of the airflow is not strong enough to de-aggregate the aggregates and accordingly they are delivered as intact aggregates. Within published specification limits, the present invention of a powder Air-razor application with an in advance prepared dose of therapeutic dry powder discloses that all of the powder, which is accessed by the moving nozzle, is indeed subjected to the necessary shearing stress to be de-aggregated.

TEST EXAMPLES

A. Test Result for Insulin, from the Group of Polypeptides

In order to study the Air-razor method applied to insulin the following in vitro experiment was performed, using a micronized, finely divided powder of human insulin comprising 50% by mass of particles with a primary particle size less than 2.16 µm and 90% by mass less than 3.81 µm.

A dose of insulin, in the form of a strip approximately 3 mm wide by 15 mm long, approximately 1034 µg mass was formed onto a substrate member using an electro-dynamic field forming method. The substrate member was then inserted into a new type of inhaler comprising an Air-razor device for de-aggregation and dispersal of a powder dose. The mouthpiece of the inhaler was connected to an Anderson impactor. Suction was then applied to the mouthpiece resulting in an air velocity of 48.2 liters per minute through the inhaler and into the impactor. The dose was dispersed in the air-stream going into the impactor and delivered in approximately one second. The powder of the dose settled in the steps of the impactor. The fine particle distribution of the delivered mass in the various steps of the impactor is shown in Table 1. Retention on the substrate member and in the relevant parts of the inhaler connected to the impactor was determined to 145.4 µg.

TABLE 1

| Anderson Impactor | Flow-corrected particle cut-off size µm | Measured mass by HPLC µg | Cumulative distribution in impactor % |
|---|---|---|---|
| Induction port + Preimpactor | | 22.20 | 100.0 |
| Step 0 | 7.66 | 0.00 | 97.5 |
| Step 1 | 6.90 | 0.00 | 97.5 |
| Step 2 | 4.44 | 93.50 | 97.5 |
| Step 3 | 3.60 | 390.20 | 87.0 |
| Step 4 | 2.53 | 311.20 | 43.1 |
| Step 5 | 1.61 | 63.10 | 8.1 |
| Step 6 | 0.84 | 8.70 | 1.0 |
| Step 7 | 0.54 | 0.00 | 0.0 |
| Filter | <0.31 | 0.00 | 0.0 |

The delivered dose was determined to 888.9 µg. All masses were determined by a HPLC method. The fine particle fraction, smaller than 5 µm, was determined to 97.5% of the delivered mass and 83.8% of total determined mass.

B. Test Result for Insulin, from the Group of Polypeptides

In order to further study the Air-razor method applied to a dose of insulin the following in vitro experiment was performed, using powder from the same batch of micronized, finely divided powder of human insulin as in experiment A. The insulin comprised 50% by mass of particles with a primary particle size less than 2.16 μm and 90% by mass less than 3.81 μm.

This time, a dose of insulin, in the form of a strip approximately 3 mm wide by 15 mm long, of approximately 1220 μg mass was formed onto a substrate member using a mechanical forming method. The dose was weighed and then deposited onto the substrate member, which was vibrated to distribute the dose evenly on the substrate and to introduce some porosity. The substrate member was then inserted into a new type of inhaler comprising an Air-razor device for de-aggregation and dispersal of a powder dose. The mouthpiece of the inhaler was connected to an Anderson impactor. Suction was then applied to the mouthpiece resulting in an air velocity of 45.4 liters per minute through the inhaler and into the impactor. The dose was dispersed in the air-stream going into the impactor and delivered in approximately one second. The powder of the dose settled in the steps of the impactor. The fine particle distribution of the delivered mass in the various steps of the impactor is shown in Table 2. Retention on the substrate member and in the relevant parts of the inhaler connected to the impactor was determined to 195.1 μg. The delivered dose was determined to 676.5 μg. All masses were determined by a HPLC method.

TABLE 2

| Anderson Impactor | Flow-corrected particle cut-off size μm | Measured mass by HPLC μg | Cumulative distribution in impactor % |
|---|---|---|---|
| Induction port + Preimpactor | | 102.7 | 100.0 |
| Step 0 | 7.90 | 2.6 | 84.8 |
| Step 1 | 7.11 | 25.0 | 84.4 |
| Step 2 | 4.58 | 108.9 | 80.7 |
| Step 3 | 3.71 | 237.0 | 64.6 |
| Step 4 | 2.61 | 146.2 | 29.6 |
| Step 5 | 1.66 | 37.3 | 8.0 |
| Step 6 | 0.87 | 9.5 | 2.5 |
| Step 7 | 0.55 | 7.3 | 1.1 |
| Filter | <0.32 | 0.0 | 0.0 |

The fine particle fraction, smaller than 5 μm, was determined to 81.5% of the delivered mass and 63.2% of total determined mass.

C. Test Result for Terbutalin, an Example of an Organic Molecule

In order to study the Air-razor method applied to a common therapeutic substance, terbutalin sulphate was selected because it represents a locally acting medicament and is readily available in powder form for use in inhalers. A Turbohaler® was procured containing 50 mg Bricanyl® (terbutalin sulphate) medicament to be used against asthma as a bronchodilating substance by stimulating $\beta_2$ receptors.

The following in vitro experiment was performed, at a different point in time from A and B, using the micronized powder of terbutalin medicament from the Turbohaler®. Doses of the powder were formed onto substrate members using an electro-dynamic field forming method. The doses were made in the form of strips approximately 3 mm wide by 15 mm long. In the present experiment a dose of approximately 2239 μg mass was used. The substrate member was positioned adjacent to a nozzle with its inlet at the same side of the substrate member as the dose. The diameter of the nozzle opening was somewhat larger than the width of the dose. The area of the nozzle inlet aperture was considerably smaller than the area occupied by the extended dose. The nozzle outlet was connected to an Anderson impactor. Suction was then applied to the nozzle outlet and the airflow was allowed to stabilize at an air velocity of 45.2 liters per minute, before the substrate member was moved past the nozzle parallel to the dose strip, such that the dose was gradually sucked up by the flowing air going into the nozzle and delivered into the impactor. The dose was delivered in approximately one second. The powder of the dose settled in the steps of the impactor. The particle distribution of the delivered mass in the various steps of the impactor is shown in Table 3. Retention on the substrate member and in the relevant parts of the inhaler connected to the impactor was determined to 151.2 μg. The delivered dose was determined to 2088 μg. All masses were determined by a HPLC method.

TABLE 3

| Anderson Impactor | Flow-corrected particle cut-off size μm | Measured mass by HPLC μg | Cumulative distribution in impactor % |
|---|---|---|---|
| Inductin port + Preimpactor | >8.0 | 516.2 | 100.0 |
| Step 0 | 7.12 | 55.6 | 75.3 |
| Step 1 | 4.59 | 121.3 | 72.6 |
| Step 2 | 3.72 | 182.1 | 66.8 |
| Step 3 | 2.61 | 483.1 | 58.1 |
| Step 4 | 1.66 | 366.6 | 35.0 |
| Step 5 | 0.87 | 277.6 | 17.4 |
| Step 6 | 0.51 | 49.4 | 4.1 |
| Step 7 | 0.34 | 9.1 | 1.7 |
| Filter | <0.3 | 27.2 | 1.3 |

The fine particle fraction, smaller than 5 μm, was determined by interpolation between steps 0 and 1 to be 73% of the delivered mass and 68% of total determined mass.

The experiments show that the Air-razor method applied to a suitably adapted and prepared dose of medicament powder formed onto a substrate member may give a very good performance in delivering the dose with a very high yield of fine particle fraction to a user. As shown in experiment B it is possible to get very good results from a simply adapted dose—in this case insulin—when applied to the Air-razor method of de-aggregation and dispersal, even if the preferred method of electrostatic and electro-dynamic field dose forming offer even better results in terms of dose de-aggregation and dispersal when applied to the Air-razor method.

By optimizing the adhesion force between particles and between particles and substrate in the deposited powder, by optimizing the powder area, by optimizing the nozzle geometry and by optimizing the speed of the relative motion between nozzle and powder, de-aggregation and thereby fine particle fraction mass of particles smaller than or equal to 5 μm, is pushed very close to 100% of the mass of the available medication powder.

Controlling "v" implicates that a most suitable dosing time interval may be defined during which delivery of a spatially extended dose should take place. The dosing time interval depends on several factors, e.g. targeted area of the airways, nominal powder load mass and type of user for the medication. From a starting point to an ending point the relative motion of dose versus nozzle must embrace the defined time interval, which normally is in a range of 0.01 to 5 seconds. The timing should be suitably selected for the application i.e. the points in time where the motion begins and ends within a time frame of a suction of air that is taking place.

It is therefore important to optimize the delivery of the dose of prepared medication powder by means of a new type of inhaler device, which takes full advantage of the powder Air-razor method. An embodiment of such a new inhaler device is disclosed in FIG. 16. Thus, the present method optimizes the delivery of the dose by taking full advantage of the described new powder Air-razor method applied to a dose of suitably prepared medication powder.

It will be understood by those skilled in the art that various modifications and changes may be made to the present invention without departure from the scope thereof, which is defined by the appended claims.

What is claimed is:

1. A method of administering a medication dose of therapeutic dry powder to a user through inhalation, comprising the steps of:
   providing a metered dose of the therapeutic dry powder on a surface of a substrate, the metered dose being arranged on the surface so as to have an elongated shape;
   providing an inhaler constructed to receive the substrate, the inhaler being constructed and arranged so as to allow relative movement between a nozzle and the substrate at a predefined speed along a path that follows a length of the elongated metered dose, so that the nozzle passes by the metered dose; and
   having the user inhale through a mouthpiece connected to the nozzle while the nozzle moves with respect to the substrate so as to release, de-aggregate, disperse into air, and deliver the therapeutic dry powder to the airways of the user over a predefined interval;
   wherein the therapeutic dry powder comprises at least one finely divided, pharmacologically active substance;
   wherein the pharmacologically active substance as it is delivered to the user comprises at least 50% fine particle fraction, with fine particle fraction defined as a fraction of the delivered pharmacologically active substance by mass with a maximum aerodynamic particle size of 5μm, where aerodynamic particle size is defined as a diameter of a spherical particle having a density of 1 g/cm$^3$ that has the same inertial properties in air as the particle of the pharmacologically active substance.

2. The method of claim 1, wherein the pharmacologically active substance is an alpha1-proteinase inhibitor.

3. The method of claim 1, wherein the pharmacologically active substance is an interleukin 1.

4. The method of claim 1, wherein the pharmacologically active substance is a parathyroid hormone.

5. The method of claim 1, wherein the pharmacologically active substance is a genotropin.

6. The method of claim 1, wherein the pharmacologically active substance consists of colony stimulating factors.

7. The method of claim 1, wherein the pharmacologically active substance is an erythropoietin.

8. The method of claim 1, wherein the pharmacologically active substance is an interferon.

9. The method of claim 1, wherein the pharmacologically active substance is calcitonin.

10. The method of claim 1, wherein the pharmacologically active substance is factor VIII.

11. The method of claim 1, wherein the pharmacologically active substance is an alpha-1-antitrypsin.

12. The method of claim 1, wherein the pharmacologically active substance is a follicle stimulating hormone.

13. The method of claim 1, wherein the pharmacologically active substance is an LHRH agonist.

14. The method of claim 1, wherein the pharmacologically active substance is IGF-I.

15. The method of claim 1, wherein the pharmacologically active substance is insulin.

16. The method of claim 1, wherein the pharmacologically active substance is a protein.

17. The method of claim 1, wherein the pharmacologically active substance is a peptide.

18. The method of claim 1, wherein the pharmacologically active substance has an electrostatic specific charge capability of at least 0.1 μC/g and a discharge rate factor of at least 0.1 s half-life period ($Q_{50}$).

19. The method of claim 1, wherein the pharmacologically active substance is systemically acting.

20. The method of claim 1, wherein the pharmacologically active substance is locally acting in the lung of the user.

21. The method of claim 1, wherein the dry powder is adapted for oral administration.

22. The method of claim 1, wherein the dry powder is adapted for nasal administration.

23. The method of claim 1, wherein the user inhales so as to produce a pressure difference within the inhaler in a range of 1–8 kPa.

24. The method of claim 1, wherein the user inhales so as to produce a pressure difference within the inhaler in a range of 1–4 kPa.

25. A method of administering a medication dose of therapeutic dry powder to a user through inhalation, comprising the steps of:
   providing a metered dose of the therapeutic dry powder on a surface of a substrate, the metered dose being arranged on the surface so as to have an elongated shape;
   providing an inhaler constructed to receive the substrate, the inhaler being constructed and arranged so as to allow relative movement between a nozzle and the substrate at a predefined speed along a path that follows a length of the elongated metered dose, so that the nozzle passes by the metered dose; and
   having the user inhale through a mouthpiece connected to the nozzle while the nozzle moves with respect to the substrate so as to release, de-aggregate, disperse into air, and deliver the therapeutic dry powder to the airways of the user over a predefined interval;
   wherein the therapeutic dry powder comprises at least one finely divided, pharmacologically active substance;
   wherein the pharmacologically active substance has an electrostatic specific charge capability of at least 0.1 μC/g and a discharge rate factor of at least 0.1 s half-life period ($Q_{50}$).

26. The method of claim 25, wherein the pharmacologically active substance is an alpha1-proteinase inhibitor.

27. The method of claim 25, wherein the pharmacologically active substance is an interleukin 1.

28. The method of claim 25, wherein the pharmacologically active substance is a parathyroid hormone.

29. The method of claim 25, wherein the pharmacologically active substance is a genotropin.

30. The method of claim 25, wherein the pharmacologically active substance consists of colony stimulating factors.

31. The method of claim 25, wherein the pharmacologically active substance is an erythropoietin.

32. The method of claim 25, wherein the pharmacologically active substance is an interferon.

33. The method of claim 25, wherein the pharmacologically active substance is calcitonin.

34. The method of claim 25, wherein the pharmacologically active substance is factor VIII.

35. The method of claim 25, wherein the pharmacologically active substance is an alpha-1-antitrypsin.

36. The method of claim 25, wherein the pharmacologically active substance is a follicle stimulating hormone.

37. The method of claim 25, wherein the pharmacologically active substance is an LHRH agonist.

38. The method of claim 25, wherein the pharmacologically active substance is IGF-I.

39. The method of claim 25, wherein the pharmacologically active substance is insulin.

40. The method of claim 25, wherein the pharmacologically active substance is a protein.

41. The method of claim 25, wherein the pharmacologically active substance is a peptide.

42. The method of claim 25, wherein the pharmacologically active substance is systemically acting.

43. The method of claim 25, wherein the pharmacologically active substance is locally acting in the lung of the user.

44. The method of claim 25, wherein the dry powder is adapted for oral administration.

45. The method of claim 25, wherein the dry powder is adapted for nasal administration.

46. The method of claim 25, wherein the user inhales so as to produce a pressure difference within the inhaler in a range of 1–8 kPa.

47. The method of claim 25, wherein the user inhales so as to produce a pressure difference within the inhaler in a range of 1–4 kPa.

48. A method of administering a medication dose of therapeutic dry powder to a user through inhalation, comprising the steps of:
providing a metered dose of the therapeutic dry powder on a surface of a substrate, the metered dose being arranged on the surface so as to have an elongated shape;
providing a means for releasing the metered dose from the substrate by subjecting an edge of the elongated metered dose to shearing stresses and inertia of an airstream sufficient to de-aggregate, release, disperse, and entrain individual particles of the metered dose into the airstream, and moving the metered dose with respect to the airstream so that the airstream moves said edge along a length of the metered dose as the dry powder is released from the substrate;
having the user inhale through a mouthpiece on the releasing means so as to inhale the de-aggregated dry powder entrained in the airstream into airways of the user;
wherein the therapeutic dry powder comprises at least one finely divided, pharmacologically active substance; and
wherein the user inhales so as to produce a pressure difference within the releasing means in a range of 1–8 kPa.

49. The method of claim 48, wherein the pharmacologically active substance as it is delivered to the user comprises at least 50% fine particle fraction, with fine particle fraction defined as a fraction of the delivered pharmacologically active substance by mass with a maximum aerodynamic particle size of 5 $\mu$m, where aerodynamic particle size is defined as a diameter of a spherical particle having a density of 1 g/cm$^3$ that has the same inertial properties in air as the particle of the pharmacologically active substance.

50. The method of claim 48, wherein the pharmacologically active substance has an electrostatic specific charge capability of at least 0.1 $\mu$C/g and a discharge rate factor of at least 0.1 s half-life period ($Q_{50}$).

51. The method of claim 48, wherein the user inhales so as to produce a pressure difference within the releasing means in a range of 1–4 kPa.

52. The method of claim 49, wherein the user inhales so as to produce a pressure difference within the releasing means in a range of 1–8 kPa.

53. The method of claim 49, wherein the user inhales so as to produce a pressure difference within the releasing means in a range of 1–4 kPa.

54. The method of claim 50, wherein the user inhales so as to produce a pressure difference within the releasing means in a range of 1–8 kPa.

55. The method of claim 50, wherein the user inhales so as to produce a pressure difference within the releasing means in a range of 1–4 kPa.

56. The method of claim 48, wherein the pharmacologically active substance is an alpha1-proteinase inhibitor.

57. The method of claim 48, wherein the pharmacologically active substance is an interleukin 1.

58. The method of claim 48, wherein the pharmacologically active substance is a parathyroid hormone.

59. The method of claim 48, wherein the pharmacologically active substance is a genotropin.

60. The method of claim 48, wherein the pharmacologically active substance consists of colony stimulating factors.

61. The method of claim 48, wherein the pharmacologically active substance is an erythropoietin.

62. The method of claim 48, wherein the pharmacologically active substance is an interferon.

63. The method of claim 48, wherein the pharmacologically active substance is calcitonin.

64. The method of claim 48, wherein the pharmacologically active substance is factor VIII.

65. The method of claim 48, wherein the pharmacologically active substance is an alpha-1-antitrypsin.

66. The method of claim 48, wherein the pharmacologically active substance is a follicle stimulating hormone.

67. The method of claim 48, wherein the pharmacologically active substance is an LHRH agonist.

68. The method of claim 48, wherein the pharmacologically active substance is IGF-I.

69. The method of claim 48, wherein the pharmacologically active substance is insulin.

70. The method of claim 48, wherein the pharmacologically active substance is a protein.

71. The method of claim 48, wherein the pharmacologically active substance is a peptide.

72. The method of claim 48, wherein the pharmacologically active substance has an electrostatic specific charge capability of at least 0.1 $\mu$C/g and a discharge rate factor of at least 0.1 s half-life period ($Q_{50}$).

73. The method of claim 48, wherein the pharmacologically active substance is systemically acting.

74. The method of claim 48, wherein the pharmacologically active substance is locally acting in the lung of the user.

75. The method of claim 48, wherein the dry powder is adapted for oral administration.

76. The method of claim 48, wherein the dry powder is adapted for nasal administration.

* * * * *